United States Patent [19]

Horn

[11] Patent Number: 4,722,933

[45] Date of Patent: * Feb. 2, 1988

[54] SUBSTITUTED 2-AMINOTETRALINS

[75] Inventor: Alan S. Horn, Noordhorn, Netherlands

[73] Assignee: Nelson Research & Development Co., Irvine, Calif.

[*] Notice: The portion of the term of this patent subsequent to Jan. 14, 2003 has been disclaimed.

[21] Appl. No.: 839,976

[22] Filed: Mar. 17, 1986

Related U.S. Application Data

[63] Continuation-in-part of Ser. No. 811,768, Dec. 20, 1985, Pat. No. 4,657,925, which is a continuation-in-part of Ser. No. 640,685, Aug. 13, 1984, Pat. No. 4,564,628.

[51] Int. Cl.[4] .................. A61K 31/38; C07D 333/00; C07D 333/56; C07D 333/12
[52] U.S. Cl. ..................... 514/438; 514/95; 514/96; 514/443; 549/6; 549/58; 549/75; 549/77
[58] Field of Search ............. 549/74, 77, 75, 6, 58; 514/438, 357, 415, 427, 399, 471, 521, 523, 95, 96, 443

[56] References Cited

U.S. PATENT DOCUMENTS 3,930,022 12/1975 Hauck et al.
4,076,843 2/1978 Hauck et al.
4,267,373 5/1981 Hauck et al.
4,314,082 2/1982 Stout.
4,410,519 10/1983 Seiler et al.
4,564,628 1/1986 Horn ................................. 549/74

FOREIGN PATENT DOCUMENTS 64964 6/1982 European Pat. Off.
1597140 9/1981 United Kingdom.

OTHER PUBLICATIONS

McDermed et al., Journal of Medicinal Chemistry, 1975, vol. 18, No. 4, pp. 362-267, (corresponding to U.S. Pat. No. 4,064,271).
Hacksell et al., Journal of Medicinal Chemistry, vol. 22, No. 12 at pp. 1469-1475, (corresponding to European Appln. 041,488).
Beauliéu et al., European Journal of Pharmacology, 105, (1984), at pp. 15-21.

Primary Examiner—Alan Siegel
Attorney, Agent, or Firm—Robert J. Baran

[57] ABSTRACT

The invention provides compounds represented by the general formula

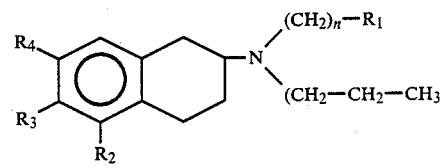

where $R_2$, $R_3$ and $R_4$ are each selected from the group consisting of H, and OA; A is H or

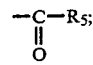

$R_5$ is selected from the group consisting of alkyl and aromatic residues; n is 2 or 3; and $R_1$ is selected from the group consisting

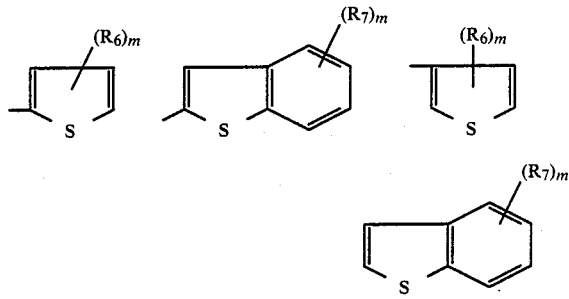

wherein $R_6$ is selected from the group consisting of halogen, hydrocarbyl and hetero atom-substituted hy- (Abstract continued on next page.)

drocarbyl, comprising from 1 to 12 carbon atoms and wherein said hetero-atoms are selected from the group consisting of halogen, nitrogen, oxygen, sulfur and phosphorus; $R_7$ is $R_6$ or H and m equals 1, 2 or 3; with the proviso that at least one of $R_2$, $R_3$ and $R_4$ is H, that at least one of $R_2$, $R_3$ and $R_4$ is not H and that $R_2$ and $R_4$ are not both OA; and pharmaceutically-acceptable salts thereof. The compounds are dopamine receptor agonists and useful for the treatment of glaucoma in mammals.

30 Claims, 2 Drawing Figures

SUBSTITUTED 2-AMINOTETRALINS

CROSS REFERENCE TO RELATED APPLICATIONS

This patent application is a continuation in part of U.S. patent application Ser. No. 811,768, filed on Dec. 20, 1986 now U.S. Pat. No. 4,657,925, which is a continuation-in-part of U.S. patent application Ser. No. 640,685, filed on Aug. 13, 1984, now U.S. Pat. No. 4,564,628, both of which applications were filed in the name of Alan S. Horn and are hereby incorporated by reference.

BACKGROUND OF THE INVENTION

1. Field of the Invention

The invention relates generally to substituted 2-aminotetralins and to processes for preparing such compounds. More particularly, the invention relates to compounds for therapeutic use, in particular in treating disorders of the central nervous, cardiovascular and endocrine systems. The compounds of this invention are also useful for alleviating glaucoma in mammals.

2. Background of the Prior Art

It is known that various hydroxylated 2-aminotetralins of the general formula

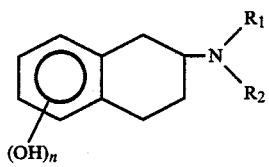

where $R_1$ and $R_2$ are saturated alkyl groups and n is 1 or 2, are dopamine receptor agonists (Mc Dermed et al., J. Med. Chem. 18, 362 (1975); Feenstra et al., Arch. Pharmacol. 313, 213 (1980).

It is also known that certain dopaminergic compounds can lower intraocular pressure in various mammals. For example, it has been suggested that bromocriptine may lower intraocular pressure in man. (See *The Lancet*, Feb. 4, 1984, "Bromocriptine Eyedrops Lower Intraocular Pressure without Affecting Prolactin Levels.", by Mekki, et al. at pages 287–288.)

Similarly, bromocriptine, as well as lergotrile and pergolide has been shown to lower the intraocular pressure of rabbits and the latter two compounds also lowered the intraocular pressure of monkeys. (See Potter, D. E. and Burke, J. A. (1982/1983), "Effects of Ergoline Derivatives on Intraocular Pressure and Iris Function in Rabbits and Monkeys", Curr. Eye Res. 2, 281–288 and Potter, D. E., Burke, J. A. and Chang, F. W. (1984), "Ocular Hypotensive Action of Ergoline Derivatives in Rabbits: Effects of Sympathectomy and Domperidone Pretreatment", Curr. Eye Res. 3, 307–314.)

It has also been shown that certain dopamine analogs of the phenylethylamine class, e.g. N-methyldopamine, N,N-dimethyl-dopamine and N,N-di-n-propyldopamine, may alter ocular function by operating through a variety of mechanisms. However, N-methyl dopamine appeared to function by suppressing aqueous humor formation. (See Potter, D. E., Burke, J. A. and Chang, F. W. (1984), "Alteration in Ocular Function Induced by Phenylethylamine Analogs of Dopamine", Curr. Eye Res. 3, 851–859.)

Finally, certain aminotetralins were shown to lower intraocular pressure in rabbits. (See Burke, J. A., Chang, F. W. and Potter, D. E. (1984), "Effects of Aminotetralins on Intraocular Pressure and Pupillary Function in Rabbits", J. Auton, Pharmacol. 4, 185–192.)

SUMMARY OF THE INVENTION

There has now been discovered certain novel compounds having the structural formula

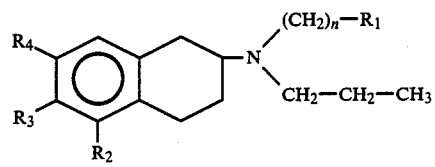

where $R_2$, $R_3$ and $R_4$ are each selected from the group consisting of H, and OA; A is H or

$R_5$ is selected from the group consisting of alkyl and aromatic residues, e.g. residues comprising from one to about twelve carbon atoms; n is 2 or 3 and $R_1$ is selected from the group consisting of

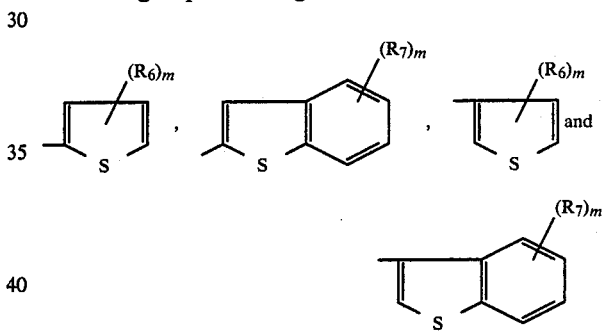

wherein $R_6$ is selected from the group consisting of halogen, hydrocarbyl and hetero atom-substituted hydrocarbyl, comprising from 1 to 12 carbon atoms and wherein said hetero-atoms are selected from the group consisting of halogen, nitrogen, oxygen, sulfur and phosphorus; $R_7$ is $R_6$ or H and m equals 1, 2 or 3; with the proviso that at least one of $R_2$, $R_3$ and $R_4$ is H, that at least one of $R_2$, $R_3$ and $R_4$ is not H, and that $R_2$ and $R_4$ are not both OA.

The compounds are useful as dopamine and, in particular, dopamine D-2 receptor agonists for the treatment of disorders of the central nervous, cardiovascular and endocrine systems such as Parkinson's disease and related disorders, hypertension and hyperprolactinemia. In particular, the compounds of this invention are useful in the treatment of glaucoma in mammals.

BRIEF DESCRIPTION OF THE DRAWING FIGURES

FIGS. 1 and 2 show the effect on pupil diameter and intraocular pressure, respectively, of monkeys that have been treated with 2-(N-n-propyl-N-2-thienylethylamino)-5-hydroxy-tetralin, the unsubstituted compound corresponding to the compounds of the present invention.

DETAILED DESCRIPTION OF THE INVENTION

Figure 1:
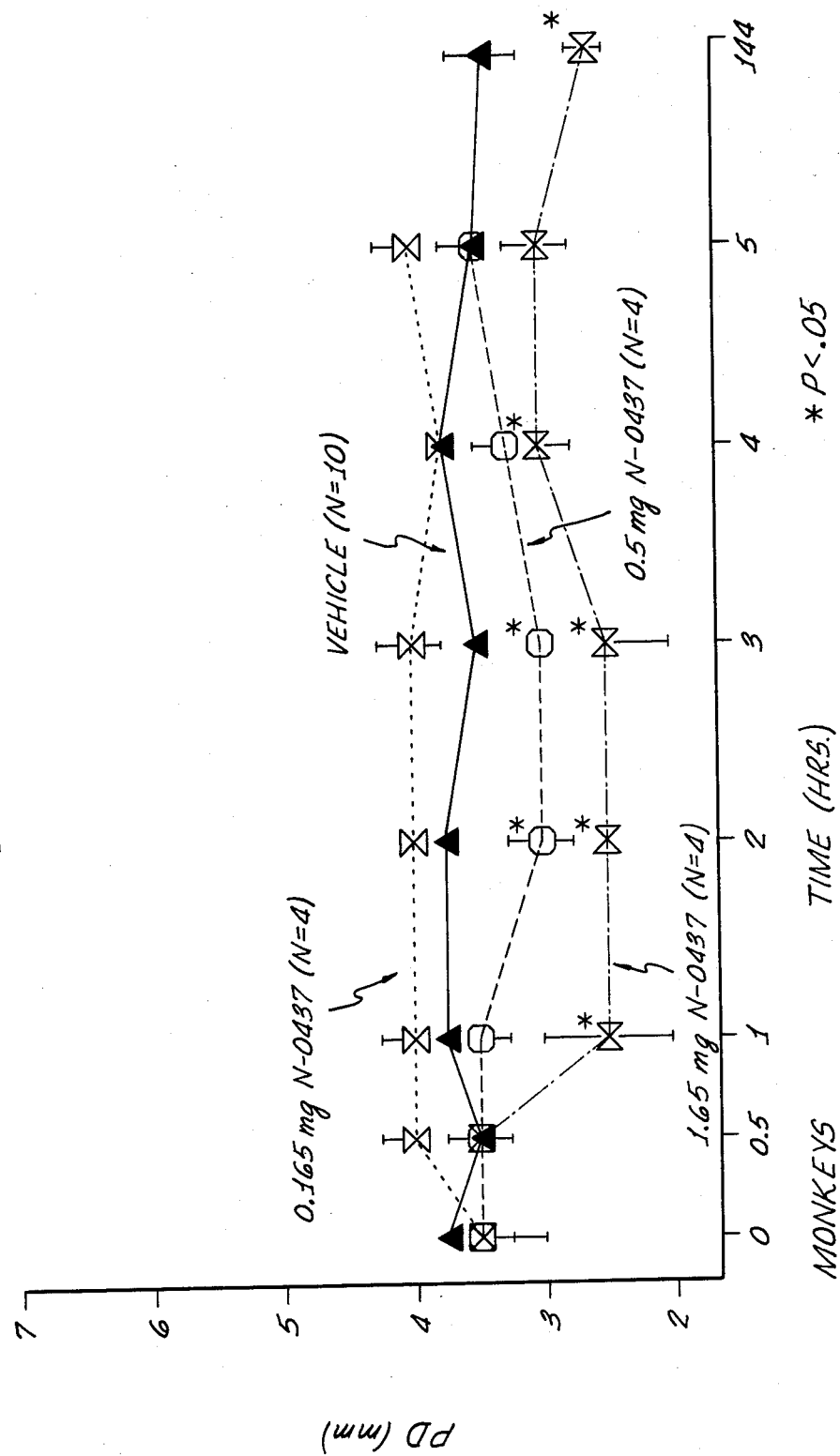

The above compounds may be made by any of the methods disclosed in U.S. patent application Ser. No. 640,685, cited above.

In particular, the compounds of this invention are prepared by reacting an alkoxy-substituted 2-(N-n-propylamino)tetralin with a thienylacetic acid substituted with the $R_6$ or

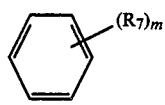

groups of choice as described further in the examples below. The resulting compound may be dealkylated to obtain the hydroxy-substituted derivative.

Preferably, $R_6$ is selected from the group consisting of an alkyl radical having from one to four carbon atoms, trifluoromethyl, halogen and phenyl. More preferably, $R_6$ is selected from the group consisting of methyl, ethyl, chloro and bromo. Preferably, $R_7$ is H.

Specific preferred compounds, which are within the scope of the above general formula include:
2-(N-n-propyl-N-2-[thienyl-4-methyl]ethylamino)-5-hydroxytetralin.
2-(N-n-propyl-N-2-[thienyl-3,4,5-trimethyl]ethylamino)-5-hydroxytetralin.
2-(N-n-propyl-N-2-[thienyl-5-chloro]ethylamino)-5-hydroxytetralin.
2-(N-n-propyl-N-2-[thienyl-4-bromo-5-methyl]ethylamino)-5-hydroxytetralin.
2-(N-n-propyl-N-2[thienyl-4-methyl-5-ethyl]ethylamino 5-hydroxytetralin.
2-(N-n-propyl-N-2-[benzothienyl]ethylamino)-5-hydroxytetralin.
2-(N-n-propyl-N-3-[benzothienyl]ethylamino)-5-hydrooxytetralin.

The prodrugs of these compounds where A is

may be prepared by treating the compound with the desired corresponding acid chloride (See Horn et al., J. Med. Chem. 25, 993, 1982).

A preferred embodiment of this invention is a method of treatment which comprises inducing a dopaminergic response by administering a therapeutically effective amount of one of the foregoing compounds to a patient. In general, a pharmacologically-effective daily dose can be from 0.01 mg./kg. to 100 mg./kg. per day, and preferably from about 0.1 mg./kg. to 25 mg./kg. per day, bearing in mind, of course, that in selecting the appropriate dosage in any specific case, consideration must be given to the patient's weight, general health, metabolism, age and other factors which influence response to the drug. A particularly preferred dose is 1.0 mg./kg. per day.

Another embodiment of this invention is the provision of pharmaceutical compositions in dosage unit form which comprise from about 2 mg. to 500 mg. of a compound of the above formula.

The pharmaceutical composition may be in a form suitable for oral use, for example, as tablets, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents, and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, for example calcium carbonate, sodium carbonate, lactose, calcium phosphate, or sodium phosphate; granulating and disintegrating agents, for example maize starch, or alginic acid; binding agents, for example starch, gelatine, or acacia; and lubricating agents, for example magnesium stearate, stearic acids, or talc. The tablets may be uncoated or they may be coated by known techniques to delay disintegration and adsorption in the gastrointestinal tract and thereby provide a sustained action over a longer period.

Formulations for oral use may also be presented as hard gelatine capsules wherein the active ingredient is mixed with an inert solid diluent, for example calcium cabonate, calcium phosphate, or kaolin, or as soft gelatine capsules wherein the active ingredient is mixed with an oil medium, for example arachis oil, liquid paraffin, or olive oil.

Aqueous suspensions contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth, and gum acacia; dispersing or wetting agents may be a naturally-occurring phosphatide, for example lecithin, or condensation products of an alkylene oxide with fatty acids, for example of polyoxyethylene stearate, or condensation products of ethylene oxide with long chain aliphatic alcohols, for example heptadecaethyleneoxycetanol, or condensation products of ethylene oxide with partial esters derived from fatty acids and a hexitol, for example, polyoxyethylene sorbitol monooleate, or condensation product of ethylene oxide with partial esters derived from fatty acids and hexitol anhydrides, for example polyoxyethylene sorbitan monooleate. The said aqueous suspensions may also contain one or more preservatives, for example ethyl, n-propyl, or p-hydroxy benzoate, one or more coloring agents, one or more flavoring agents, and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, may also be present.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol.

The pharmaceutical compositions may be tableted or otherwise formulated so that for every 100 parts by weight of the composition there are present between 5 and 95 parts by weight of the active ingredient and preferably between 25 and 85 parts by weight of the active ingredient. The dosage unit form will gnerally contain between about 1 mg. and about 100 mg. of the active ingredient of the formula stated above.

From the foregoing formulation discussion it is apparent that the compositions of this invention can be administered orally or parenterally. The term parenteral as used herein includes subcutaneous injection, intravenous, intramuscular, or intrasternal injection or fusion techniques.

Even more preferably, the method of the present invention comprises administering substituted 2-(N-propyl-N-2-thienylethylamino)-5-hydroxytetralin to the eye of a mammal to reduce intraocular pressure. Moreover, the levo (−) isomers of these substituted compounds are believed to be the more active isomers for use in the method of the present invention.

Suitable opthalmic carriers are known to those skilled in the art and all such conventional carriers may be employed in the present invention. Thus, a particular carrier may take the form of a sterile opthalmic ointment, cream, gel, solution, or dispersion and preferably a solution. Also including as suitable ophthalmic carriers are slow releasing polymers, e.g. "Ocusert" polymers, "Hydron" polymers, etc. Stabilizers may also be used as, for example, chelating agents, e.g. EDTA. Anti-oxidants may also be used, e.g. sodium bisulfite, sodium thiosulfite, 8-hydroxy quinoline or ascorbic acid. Sterility typically will be maintained by conventional opthalmic preservatives, e.g. chlorbutanol, benzalkonium chloride, cetylpyridinium chloride, phenyl mercuric salts, thimerosol, phenethyl alcohol, etc., for aqueous formulations, and used in amounts which are non-toxic and which generally vary from about 0.001 to about 0.1% by weight of the aqueous solution. Conventional preservatives for ointments include methyl and propyl parabens. Typical ointment bases include white petrolatum and mineral oil or liquid petrolatum. However, preserved aqueous carriers are preferred. Solutions may be manually delivered to the eye in suitable dosage form, e.g., eye drops, or delivered by suitable microdrop or spray apparatus typically affording a metered dose of medicament. Examples of suitable opthalmic carriers or stabilizers include sterile, substantially isotonic, aqueous solutions containing minor amounts, i.e., less than about 5% by weight hydroxypropylmethylcellulose, polyvinyl alcohol, carboxymethylcellulose, hydroxyethylcellulose, glycerine, EDTA, sodium bisulfite and ascorbic acid.

The amount of active compound to be used in the therapeutic treatment of glaucoma will vary with the age of the patient and the severity of the glaucoma. Generally, a dose level of one or two drops of the foregoing aqueous solution 1–4 times daily would be a suitable dosage amount. Generally, the concentration of active compound will vary between about 0.001 and about 5% and preferably between about 0.05 and about 1% (wt./v calculated on the basis of the free base) of said opthalmic composition.

Preferably, the opthalmic composition of this invention should have a pH within the range of about 4.0 to 9.0 when intended for topical application. Above and below this pH range the solution may irritate and sting the eye of the user. The solutions of the present invention may be maintained between about pH 4.0 and 7.5 with suitable amounts of buffering agents including borate, carbonate, phosphate. Tris(hydroxymethyl aminomethane), acetate and citrate buffers.

A preferred opthalmic composition is a preserved aqueous solution containing the following ingredients at approximately the indicated concentration.

TABLE

| | |
|---|---|
| Active compound | 0.001–1 wt. % |
| Stabilizer | 0.01–0.1 wt. % |
| Preservative | 0.005–0.5 wt. % |
| Buffer (sufficient to maintain pH between about 4.0 and 7.5) | 0.1–0.001 M |
| NaCl qs. ad. | (isotonic) |
| Water qs. ad. | 100% |

To illustrate the manner in which the invention may be carried out, the following examples are given. It is understood, however, that the examples are for the purpose of illustration and the invention is not be regarded as limited to any of the specific materials or conditions therein.

EXAMPLE 1

Preparation of
2-(N-n-propyl-N-2-[thienyl-4-methyl]ethylamino)-5-hydroxytetralin A mixture of 2-(N-n-propylamino)-5-methoxytetralin, 4-methyl-2-thienylacetic acid (Clemence et al. Eur. J. Med. Chem. 9 390–396, 1974) and trimethylaminoborohydride in dry xylene was refluxed under an atomsphere of nitrogen as described by Horn et al Pharm. Weekbld. Sci. Ed. 7 208–211, 1985. The resulting methoxy intermediate was demethylated using boron tribromide as described in the above article to yield the desired end product.

EXAMPLE 2

Preparation of
2-(N-n-propyl-N-2-[thienyl-3,4,5-trimethyl]ethylamino)-5-hydroxytetralin The end product was obtained using the above method and 3,4,5-trimethyl-2-thienylacetic acid (Gronwitz and Torbjorn, Acta Chem. Scand. Ser B., B 29, 818–826, 1975).

EXAMPLE 3

Preparation of
2-(N-n-propyl-N-2-[thienyl-5-chloro]ethylamino)-5-hydroxytetralin The end product was obtained using the above method and 5-chloro-2-thienylacetic acid (Ford et al. J. Am. Chem. Soc. 72 2109–2112, 1950).

EXAMPLE 4

Preparation of
2-(N-n-propyl-N-2-[thienyl-4-bromo-5-methyl]e-
thylamino)-5-hydroxytetralin The end product was obtained using the above method and 4-bromo-5-methyl-2-thienylacetic acid (Gronwitz and Torbjorn, Acta Chem. Scand. Ser B., B. 29, 818–826, 1975).

EXAMPLE 5

Preparation of
2-(N-n-propyl-N-2[thienyl-4-methyl-5-ethyl]e-
thylamino-5-hydroxytetralin The end product was obtained by using the above method and 4-methyl-5-ethyl-2-thienylacetic acid (Nguyen and Hauptmann, Z. Chem. 13 57–58, 1973).

EXAMPLE 6

Prodrug esters of the compounds of EXAMPLES 1–5 are prepared by reacting the phenols with desired corresponding acid chloride (Horn et al I. Med. Chem. 25 993, 1982).

The unsubstituted 2-(N-n-propyl-N-2-thienyle-thylamino)-5-hydroxy-tetralin active compound) was tested for reducing the intraocular pressure in mammals, as described below.

Male, albino New Zealand rabbits, female *Cebus apella* monkeys and cats of mixed sexes were used for this test. Rabbits were used primarily to screen for undue ocular toxicity of the active compound before conducting experiments in monkeys. Cats were used to localize the site and mechanism of action of the active compound as either ganglionic, prejunctional or post-junctional.

A racemic mixture of the active compound was dissolved in distilled water (vehicle) on the day of the experiment. Solutions were administered in a masked manner, that is, solutions were prepared by a person that was neither involved in drug administration nor measurement of intraocular pressure (IOP) and pupil diameter (PD). The solution of the active compound was applied unilaterally with the contralateral (fellow) eye receiving vehicle only. Five monkeys were treated bilaterally with vehicle; one to two vehicle-treated monkeys were included each time a different dose of the active compound was used. Doses of active compound tested were: 0.165, 0.5 and 1.65 mg.

Figure 2:
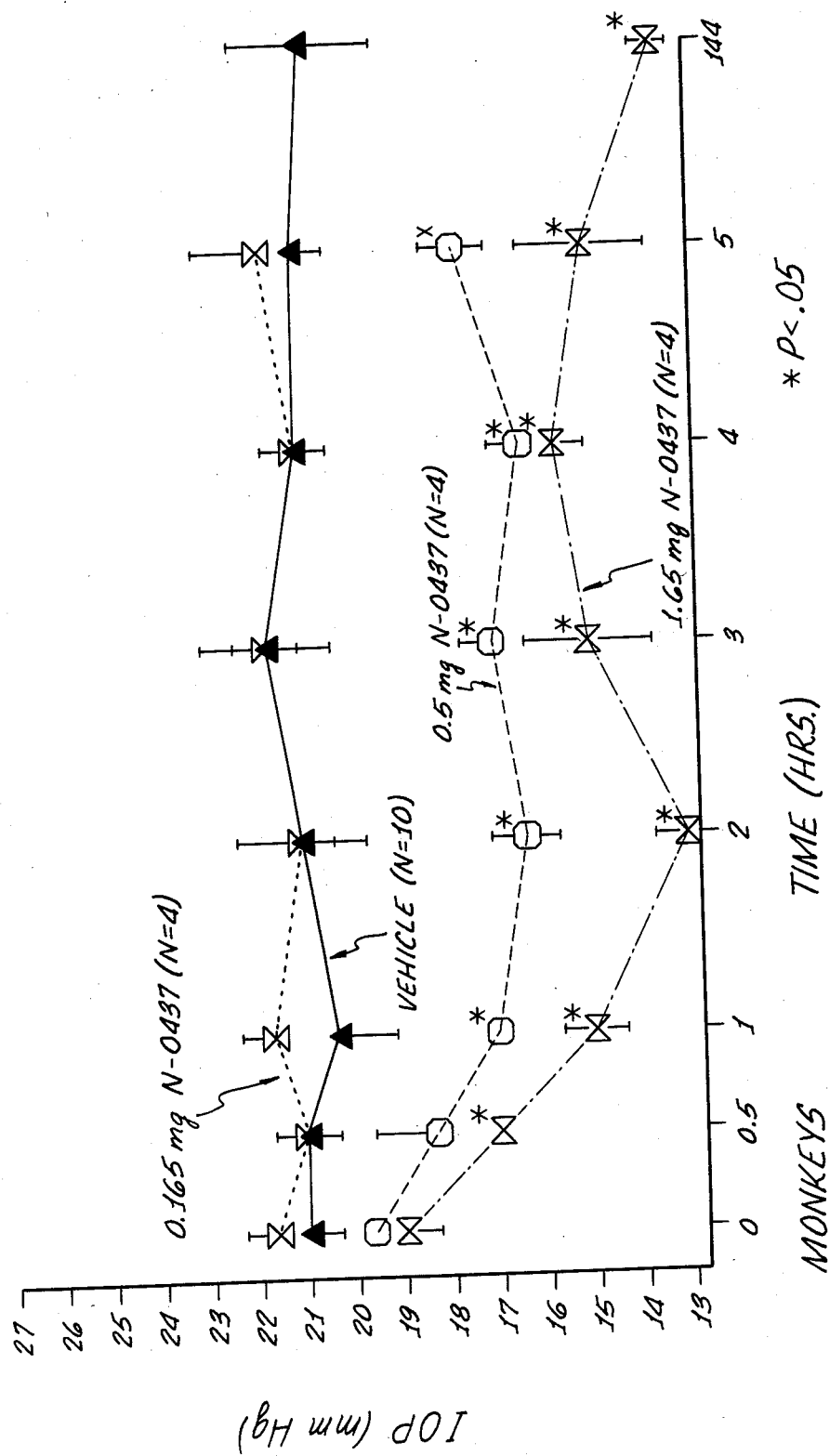

Horizontal PD was measured utilizing an Optistick. After taking two baseline (0 time) measurements, aliquots (50 l) of the solution of the active compound and/or vehicle, only, were administered topically. Subwsequently, IOP and PD measurements were made at 0.5, 1, 2, 3, 4 and 5 hours post drug. Additional readings were taken on subsequent days when it became apparent that the ocular effects of the active compound were protracted. Gross observations were made regarding signs of ocular irritation and systemic effects. The results were reported in FIGS. 1 and 2.

The active compound produced dose-related ocular hypotension, miosis and ptosis in monkeys at doses of 0.5 and 1.65 mg topically. Shortly after topical administration there was evidence of ocular irritation in the form of tearing, exudate and hyperemia. Subsequently, there was evidence of clouding of the cornea, miosis and ptosis. After the initial phase of exudation, the hyperemia, ptosis and miosis persisted for hours to days. At 144 hours and beyond, there were also signs of sympathetic suppression to extraocular (ptosis) and intraocular (miosis and hyperemia) structures.

The active compound also produced dose-related suppression of neuronally mediated contractions of the nictitans with minimal effects on contractions induced by norepinephrine intra-arterially (i.a.). This test is described in Potter, D. E. and Burke, J. A. (1984), "An In Vivo Model for Discriminating $_2$ and DA$_2$-Adrenoceptor Activity in an Ocular Adnexa; Utility of the Cat Nictitating Membrane Preparation", Curr. Eye Res. 3, 1289–1298. The inhibitory effects of the active compound were fully reversible within 106 minutes after the last dose. Pretreatment with domperidone i.a. had no effect on contractions elicited by neuronal stimulation and by exogenous norepinephrine but produced a 100 fold shift in the inhibitory index of the active compound on neuronally mediated contractions of the nictitans.

These results demonstrate that the active commpound, a DA$_2$ agonist, lowered IOP and reduced miosis and ptosis in monkeys. The IOP and pupillary responses to the active compound responses occurred within several hours and, depending on the dose, persisted for many days. The acute response of the cat nictitans to the active compound i.a. was reversible and antagonized competitively by domperidone. These data would suggest that the acute phase of action is an action on DA$_2$ receptors in the periphery because the relatively selective antagonist, domperidone, penetrates the pial-glial barrier poorly. The chronic response to the active compound in monkeys would also appear to be due to suppression of sympathetic neuronal function and would appear to be slowly reversible. The prolonged phase of action is reminiscent of a guanethidine- or reserpine-like effect.

In summary, the active compound is a DA$_2$ agonist that lowers IOP in monkeys. Although it produces moderate ocular irritation at high doses, the compound provides a very prolonged occular hypotensive action.

EXAMPLE 7

The compounds of EXAMPLES 1 to 6 are formulated into compositions having ingredients and concentrations given in the above Table. When these compositions, which are derivatives of the active compound, are introduced into the eye of a mammal and tested, as was the active compound, the intraocular pressure is reduced.

While particular embodiments of the invention have been described it will be understood of course that the invention is not limited thereto since many obvious modifications can be made and it is intended to include within this invention any such modifications as will fall within the scope of the appended claims.

What is claimed is:

1. A compound having the structural formula

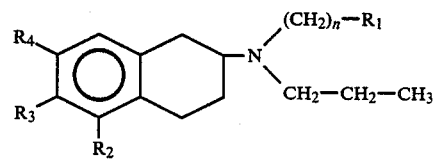

where R$_2$, R$_3$ and R$_4$ are each selected from the group consisting of H, and OA; A is H or

$R_5$ is selected from the group consisting of alkyl and aromatic residues; n is 2 or 3; and $R_1$ is selected from the group consisting

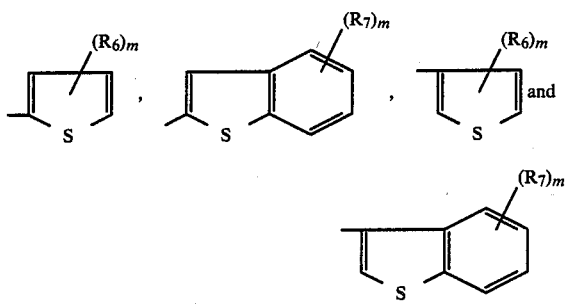

wherein $R_6$ is selected from the group consisting of halogen, hydrocarbyl and hetero atom-substituted hydrocarbyl, comprising from 1 to 12 carbon atoms and wherein said hetero-atoms are selected from the group consisting of halogen, nitrogen, oxygen, sulfur and phosphorus; $R_7$ is $R_6$ or H and m equals 1, 2 or 3; with the proviso that at least one of $R_2$, $R_3$ and $R_4$ is H, that at least one of $R_2$, $R_3$ and $R_4$ is not H and that $R_2$ and $R_4$ are not both OA; and pharmaceutically-acceptable salts thereof.

2. The compound of claim 1, where $R_4$ is H and $R_2$ $R_3$ are OH.

3. The compound of claim 1, where $R_2$ is H and $R_3$ and $R_4$ are OH.

4. The compound of claim 1, where $R_3$ and $R_4$ are H and $R_2$ is OH.

5. The compound of claim 1, where $R_2$ and $R_3$ are H and $R_4$ is OH.

6. The compound of claim 1, where n is 2.

7. The compound of claim 1 wherein $R_2$ is OH or

wherein $R_5$ is selected from the group consisting of alkyl and aromatic residues comprising from one to about twelve carbon atoms, $R_3$ and $R_4$ are H and n is 2.

8. The compound of claim 7 wherein $R_6$ is selected from the group consisting of an alkyl radical having from one to four carbon atoms, trifluoromethyl, halogen and phenyl, and $R_7$ is hydrogen.

9. The compound of claim 7 wherein $R^1$ is

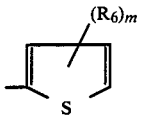

10. The compound of claim 9 whrein $R_6$ is methyl and m is 1.

11. The compound of claim 9 wherein $R_6$ is methyl and m is 3.

12. The compound of claim 9 wherein $R_6$ is chloro and m is 1.

13. The compound of claim 9 wherein $R_6$ is selected from the group consisting of bromo and methyl and m is 2.

14. The compound of claim 9 wherein $R_6$ is selected from the group consisting of methyl and ethyl and m is 2.

15. A method comprising:
    inducing a dopaminergic response in a patient by administering a pharmacologically-effective amount of a compound of claim 1.

16. The method of claim 15, wherein the compound is a compound of claim 7.

17. The method of claim 15, wherein the compound is a compound of claim 8.

18. The method of claim 15, wherein the compound is a compound of claim 10.

19. The method of claim 15, wherein the compound is a compound of claim 11.

20. The method of claim 15, wherein the compound is a compound of claim 12.

21. The method of claim 15 wherein the compound is a compound of claim 13.

22. The method of claim 15 wherein the compound is a compound of claim 14.

23. A method for reducing the intraocular pressure in mammals which comprises administering an effective amount of a compound of claim 1.

24. A method according to claim 23 wherein the compound is a compound of claim 7.

25. A method according to claim 23 wherein the compound is a compound of claim 8.

26. A method according to claim 23 wherein the compound is a compound of claim 10.

27. A method according to claim 23 wherein the compound is a compound of claim 11.

28. A method according to claim 23 wherein the compound is a compound of claim 12.

29. A method according to claim 23 wherein the compound is a compound of claim 13.

30. A method according to claim 23 wherein the compound is a compound of claim 14.

* * * * *